(12) United States Patent
Li

(10) Patent No.: US 9,211,357 B1
(45) Date of Patent: Dec. 15, 2015

(54) PUMP TYPE AROMA DIFFUSER

(71) Applicant: Puzhen Life Co., Ltd, Hong Kong (HK)

(72) Inventor: Dong Sheng Li, Hong Kong (HK)

(73) Assignee: PUZHEN LIFE CO., LTD, Hong Kong (HK)

( * ) Notice: Subject to any disclaimer, the term of this patent is extended or adjusted under 35 U.S.C. 154(b) by 0 days.

(21) Appl. No.: 14/841,724

(22) Filed: Sep. 1, 2015

(30) Foreign Application Priority Data

Aug. 14, 2015 (HK) .................................. 15107865

(51) Int. Cl.
*B01F 3/04* (2006.01)
*A61M 11/06* (2006.01)
*A61L 9/14* (2006.01)

(52) U.S. Cl.
CPC *A61L 9/14* (2013.01); *A61M 11/06* (2013.01); *B01F 3/04021* (2013.01); *B01F 3/04056* (2013.01); *B01F 3/04248* (2013.01); *B01F 2215/009* (2013.01)

(58) Field of Classification Search
CPC .... B01F 3/04; B01F 3/04007; B01F 3/04021; B01F 3/04049; B01F 3/04056; A61M 11/00; A61M 11/06

USPC ........ 261/76, 78.2, 118, DIG. 75; 239/8, 338; 422/124
See application file for complete search history.

(56) References Cited

U.S. PATENT DOCUMENTS 2,826,454 A * 3/1958 Coanda ................. A61M 11/06
128/200.18
6,645,436 B2 * 11/2003 Davis ....................... A61L 9/14
239/338

* cited by examiner

*Primary Examiner* — Robert A Hopkins

(57) ABSTRACT

The present invention provides a pump type aroma diffuser including an essential oil bottle for containing essential oil and a gasification assembly connected with an open end of the essential oil bottle. The gasification assembly includes a gasification cavity, as well as an air nozzle and an essential oil nozzle which are installed on the cavity wall of the gasification cavity. The air nozzle and the essential oil nozzle are interconnected with the gasification cavity. The pump type aroma diffuser also includes a guide assembly which covers the gasification cavity and is configured to guide aroma. The guide assembly has a concentrated fog outlet for exhausting aroma, a first intake backflow channel and a second intake backflow channel which extend from the concentrated fog outlet to two different directions. The tail ends of the first intake backflow channel and the second intake backflow channel extend into the gasification cavity.

10 Claims, 4 Drawing Sheets

PUMP TYPE AROMA DIFFUSER

CROSS-REFERENCE TO RELATED APPLICATIONS

This application claims the benefit of Hong Kong Patent Application No. HK15107865.0 filed on Aug. 14, 2015; the contents of which is hereby incorporated by reference.

TECHNICAL FIELD

The present invention relates to the field of aroma diffusers, in particular to a pump type aroma diffuser by which aroma is diffused smoothly.

DESCRIPTION OF THE RELATED ART

With continuous improvement of living level of people, more and more people began to make use of essential oil for purposes of soothing nerves, delighting the mood or comforting the soul. In most of pump type aroma diffusers used at present, liquid essential oil is converted into aerial fog according to a Venturi effect. In the process of diffusion, a part of the aerial fog will be converted into liquid and flow back to the aroma diffuser. Existing aroma diffusers, in general, have only one channel which is used for both diffusion of aerial fog and backflow of liquid. When the aerial fog and the liquid encounter in the channel, on one hand, the liquid may form air bubbles blocking the air inlet and thus the aerial fog may fail to be exhausted, and on the other hand, due to the action of airflow, the liquid may fail to flow back and be accumulated near the fog outlet, and then will overflow from the aroma diffuser when accumulated to a certain degree, leading to failure of aromatherapy, waste of essential oil and pollution of environment.

Hence, a pump type aroma diffuser with smooth aroma diffusion and easy backflow of essential oil is needed.

SUMMARY OF THE INVENTION

The present invention aims at providing a pump type aroma diffuser by which the aroma is diffused smoothly and liquid essential oil is convenient to flow back. Therefore, the pump type aroma diffuser provided by the present invention comprises an essential oil bottle for containing essential oil, a gasification assembly connected with an open end of the essential oil bottle and a guide assembly. The gasification assembly comprises a gasification cavity for guiding aroma, an air nozzle and an essential oil nozzle. The air nozzle and the essential oil nozzle are installed on the cavity wall of the gasification assembly and are interconnected with the gasification cavity. The guide assembly covers the gasification cavity and comprises a concentrated fog outlet for exhausting aroma. The guide assembly further comprises a first intake backflow channel and a second intake backflow channel which extend from the concentrated fog outlet to two different directions. The tail ends of the first intake backflow channel and the second intake backflow channel extend into the gasification cavity.

As a preferred embodiment, the pump type aroma diffuser also comprises a gasification cavity cover which covers the gasification assembly and the guide assembly and is used for sealing The gasification cavity cover is has a cover plate. The cover plate has an aroma diffusion hole, and aroma is diffused out of the pump type aroma diffuser from the aroma diffusion hole.

As a preferred embodiment, the gasification cavity cover also comprises a first annular sealing layer and a second annular layer which extend out from one side of the cover plate. The first sealing layer is configured to seal the guide assembly and the second sealing layer is configured to seal the gasification assembly.

As a preferred embodiment, the guide assembly comprises a support plate covering the gasification cavity and a sleeve installed on the support plate and close to one side of the gasification cavity cover. The concentrated fog outlet is located at the inner wall of the sleeve.

As a preferred embodiment, the support plate comprises a first plate and a second plate which are butted with each other. The sleeve is installed on the second plate. The first intake backflow channel and the second intake backflow channel respectively penetrate through the first plate and the second plate in a circular arc shape from both sides of the first plate. The first intake backflow channel and the second intake backflow channel are interconnected with the concentrated fog outlet on the inner wall of the sleeve.

As a preferred embodiment, one end, which is interconnected with the gasification cavity, of the first intake backflow channel has a first intake backflow hole. One end, which is interconnected with the gasification cavity, of the second intake backflow channel has a second intake backflow hole. Positions of the first intake backflow hole and the second intake backflow hole are interlaced with each other.

As a preferred embodiment, the bottom of the gasification cavity has an annular protruding portion which extends into the open end of the essential oil bottle and is butted with the open end of the essential oil bottle, so that a part of non-gasified essential oil can flow back to the essential oil bottle.

As a preferred embodiment, the gasification assembly also comprises an oil guide pipe disposed in the essential oil bottle. One end of the oil guide pipe is connected with the essential oil nozzle, and another end of the oil guide pipe is inserted into the bottom of the essential oil bottle.

As a preferred embodiment, the gasification assembly also comprises a mounting wall for the essential oil bottle to be mounted on The outer side surface of the open end of the essential oil bottle has first threads, and the inner side of the mounting wall has corresponding second threads. The open end of the essential oil bottle is connected to the mounting wall via threaded connection.

As a preferred embodiment, the air nozzle is interconnected with the air inlet channel. The essential oil nozzle is interconnected with the essential oil bottle through the oil guide pipe. The exhaust direction of airflow of the air nozzle is perpendicular to the jet direction of the essential oil jetted from the essential oil nozzle. The air nozzle and/or the essential oil nozzle are/is made of stainless steel.

When the aroma diffuser of the present invention is implemented, aroma can be diffused smoothly since there are two intake backflow channels and the two intake backflow channels are asymmetric. Essential oil converted into liquid is easier to flow back to the essential oil bottle. Thus the blocking problem of the channels can be avoided, and also the essential oil will not be wasted.

DETAILED DESCRIPTION OF PREFERRED EMBODIMENTS

Figure 1:
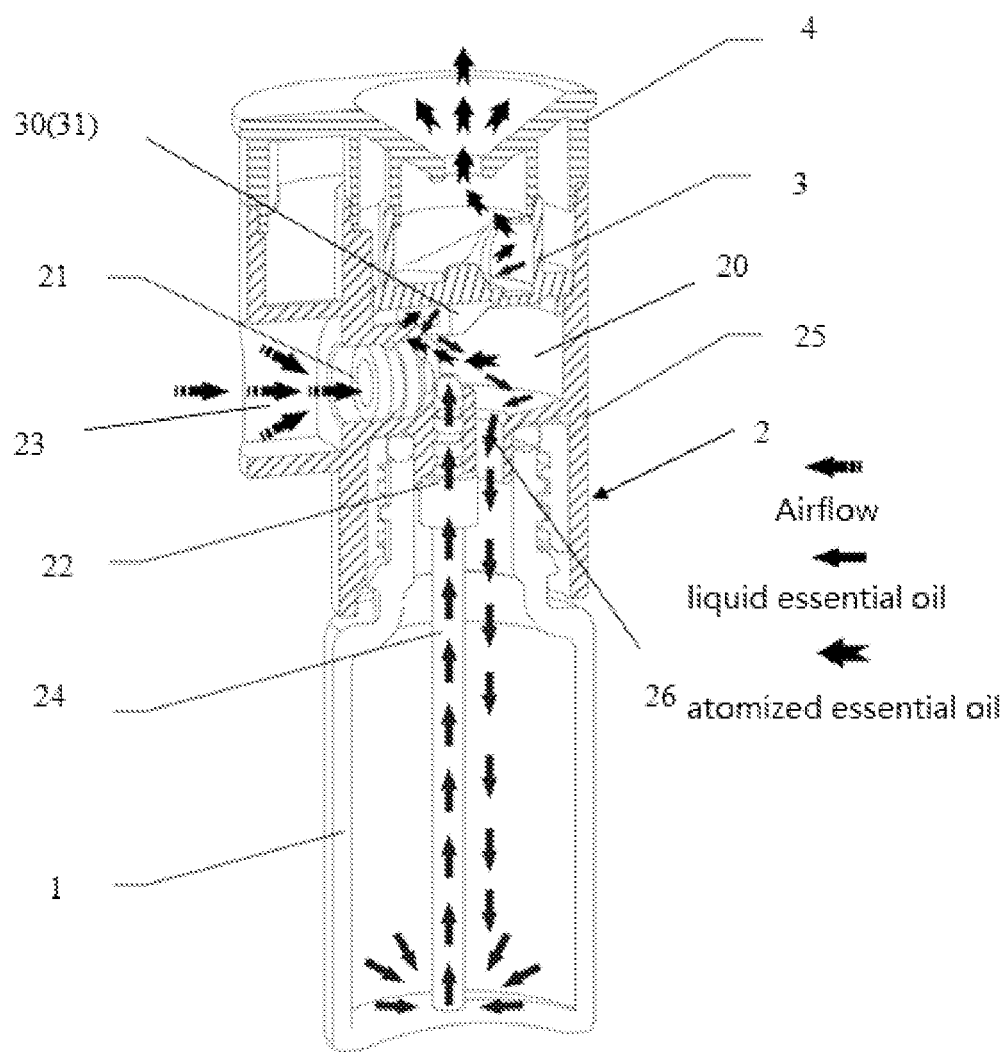
FIG. 1 is a sectional view of partial structure of the aroma diffuser of the present invention.

Referring to FIG. 1, the present invention provides an aroma diffuser comprising an essential oil bottle 1, a gasification assembly 2, a guide assembly 3 and a gasification cavity cover 4. The gasification assembly 2 is connected to the open end of the essential oil bottle 1. The guide assembly 3 is covered by the gasification assembly 2. The gasification cavity cover 4 is configured to further cover the gasification assembly 2 and the guide assembly 3.

The gasification assembly 2 comprises a gasification cavity 20, an air nozzle 21, an essential oil nozzle 22, an air inlet channel 23 interconnected with the inlet end of the air nozzle 21 and an oil guide pipe 24 directly interconnected with the inlet end of the essential oil nozzle 22. The air nozzle 21 and the essential oil nozzle 22 are installed on the cavity wall of the gasification cavity 20. The gasification assembly 2 also comprises an air pump which is used to form airflow and jet the airflow out from the air nozzle 21. The gasification assembly 2 further comprises an essential oil pump used for extracting essential oil in the essential oil bottle and jet the essential oil out from the essential oil nozzle 22. The processes of forming the airflow by using the air pump and extracting the essential oil by using the essential oil pump are well known in the art, and are not the main points of the present invention, and thus will not be described in detail. In this embodiment, the oil guide pipe 24 is disposed in the essential oil bottle 1, wherein one end of the oil guide pipe 24 is interconnected with the inlet end of the essential oil nozzle 22, and the other end thereof is inserted to the bottom of the essential oil bottle 1 but is not in contact with the bottle wall. The outlet end of the air nozzle 21 and the outlet end of the essential oil nozzle 22 are interconnected with the gasification cavity 20 respectively. The exhaust direction of airflow of the air nozzle 21 is perpendicular to the jet direction of essential oil jetted from the essential oil nozzle 22. The relative positions of the air nozzle 21 and the essential oil nozzle 22 are very close so that the essential oil in the essential oil bottle 1 can be easily extracted via the oil guide pipe 24 and then be atomized.

The gasification assembly 2 also comprises a mounting wall 25 which is configured to connect the open end of the essential oil bottle 1. The mounting wall 25 is cylindrical and located outside the gasification cavity 20. In this embodiment, the essential oil bottle 1 is detachably connected to the mounting wall 25 via threaded connection. The outer side surface of the open end of the essential oil bottle 1 has first threads (external threads). The inner surface of the mounting wall 25 has corresponding second threads (internal threads). The first threads are rotatably connected with the second threads.

Figure 2:
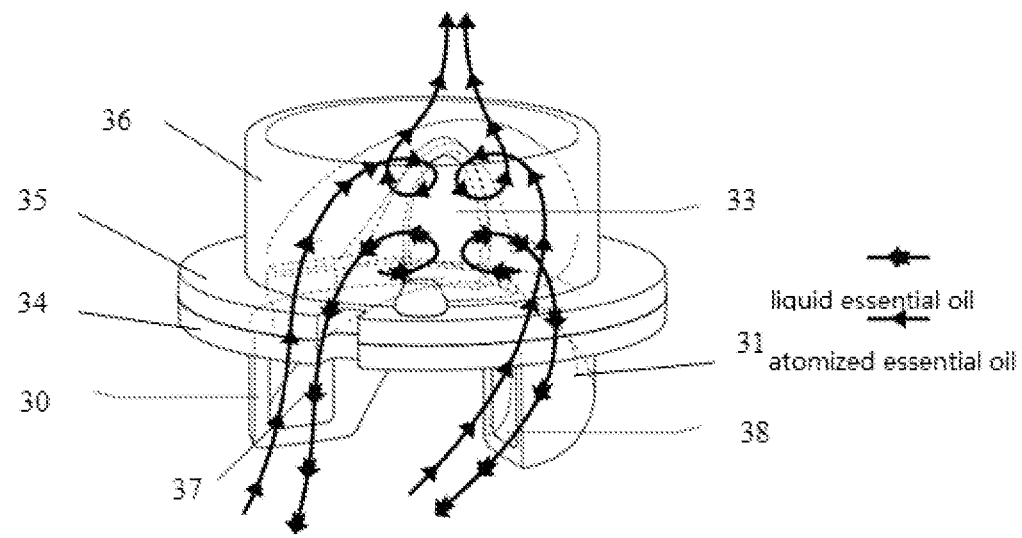
FIG. 2 is a structural schematic diagram of the guide assembly of the aroma diffuser of the present invention.

By reference to FIG. 1 and FIG. 2, the guide assembly 3 comprises a support plate connected with the cavity wall of the gasification cavity 20, a concentrated fog outlet 33, a first intake backflow channel 30 and a second intake backflow channel 31. The first intake backflow channel 30 and the second intake backflow channel 31 extend out from the concentrated fog outlet 33 to two different directions. The first intake backflow channel 30 and the second intake backflow channel 31 penetrate through the support plate and further extend into the gasification cavity 20, and are interconnected with the gasification cavity 20. In this embodiment, the support plate comprises a first plate 34 and a second plate 35 which are butted with each other. The second plate 35 has a sleeve 36. The concentrated fog outlet 33 is positioned on the inner wall of the sleeve 36. The first intake backflow channel 30 and the second intake backflow channel 31 respectively penetrate through the first plate 34 and the second 35 in a circular arc shape and are further asymmetrically coiled on the first plate 34. One end, which is interconnected with the gasification cavity 20, of the first intake backflow channel 30 has a first intake backflow hole 37. One end, which is interconnected with the gasification cavity 20, of the second intake backflow channel 31 has a second intake backflow hole 38. The direction of aroma inlet or the direction of essential oil backflow in the first intake backflow hole 37 and the second intake backflow hole 38 are interlaced with each other. By using two intake backflow channels, aerial fog exhausted upwards can be prevented from forming air bubbles to block the intake backflow channels when encountering with liquid flowing back downwards, so that the aroma can be exhausted smoothly and liquid can flow back to the essential oil bottle 1 as well. In the meantime, the bottom of the gasification cavity 20 has an annular protruding portion 27 which extends to the open end of the essential oil bottle and is butted with the open end of the essential oil bottle 1, so that a part of non-gasified essential oil can flow back to the essential oil bottle 1.

Figure 3:
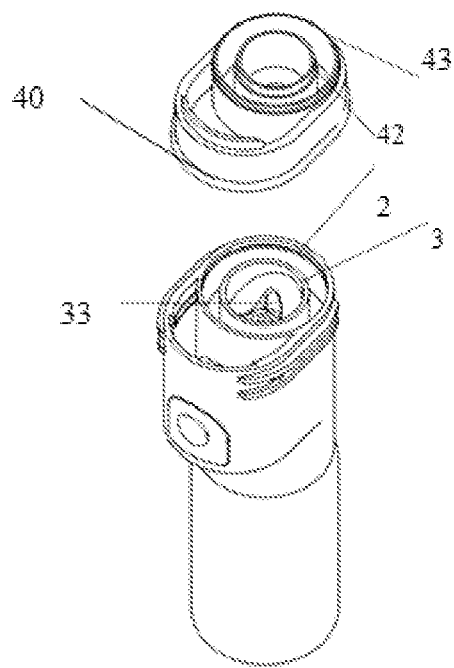
FIG. 3 is a structural schematic diagram of the gasification cavity cover and the sealing layers of the aroma diffuser of the present invention.
Figure 4:
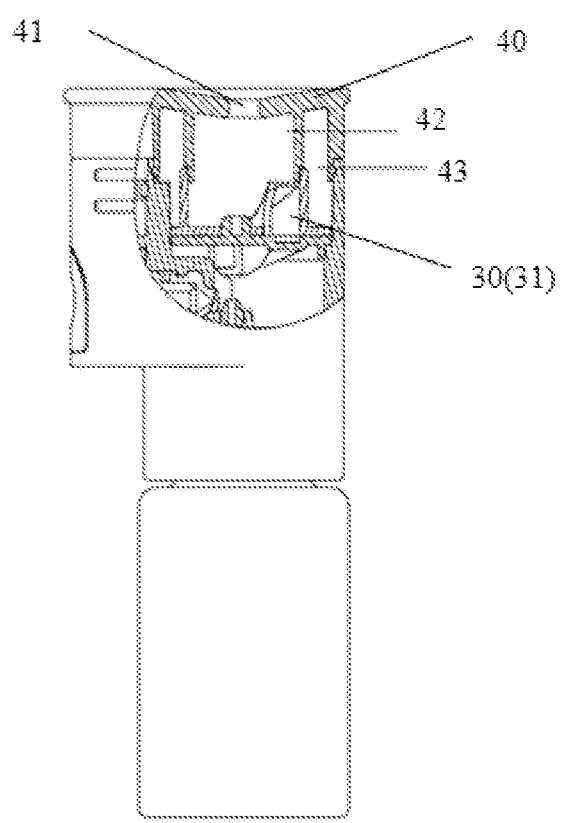
FIG. 4 is a sectional view of the gasification cavity cover and the sealing layers of the aroma diffuser of the present invention.

By reference to FIG. 3 and FIG. 4, the gasification cavity cover 4 has a cover plate 40. The cover plate 40 covers the guide assembly 3 and comprises a conical aroma diffusion hole 41 thereon. The aroma is diffused out of the aroma diffuser from the aroma diffusion hole 41. The gasification cavity cover 4 further comprises a first sealing layer 42 and a second sealing layer 43 which extend out from the cover plate 40. The first sealing layer 42 is butted with the inner wall of the sleeve 36 and is configured to seal the guide assembly 3; and the second sealing layer 43 is butted with the inner wall of the gasification assembly 2 and is configured to seal the gasification assembly 2, for a purpose of preventing the atomized aroma from diffusing from the connection parts of the gasification cavity cover 4, the gasification assembly 2 and the guide assembly 3.

Figure 5:
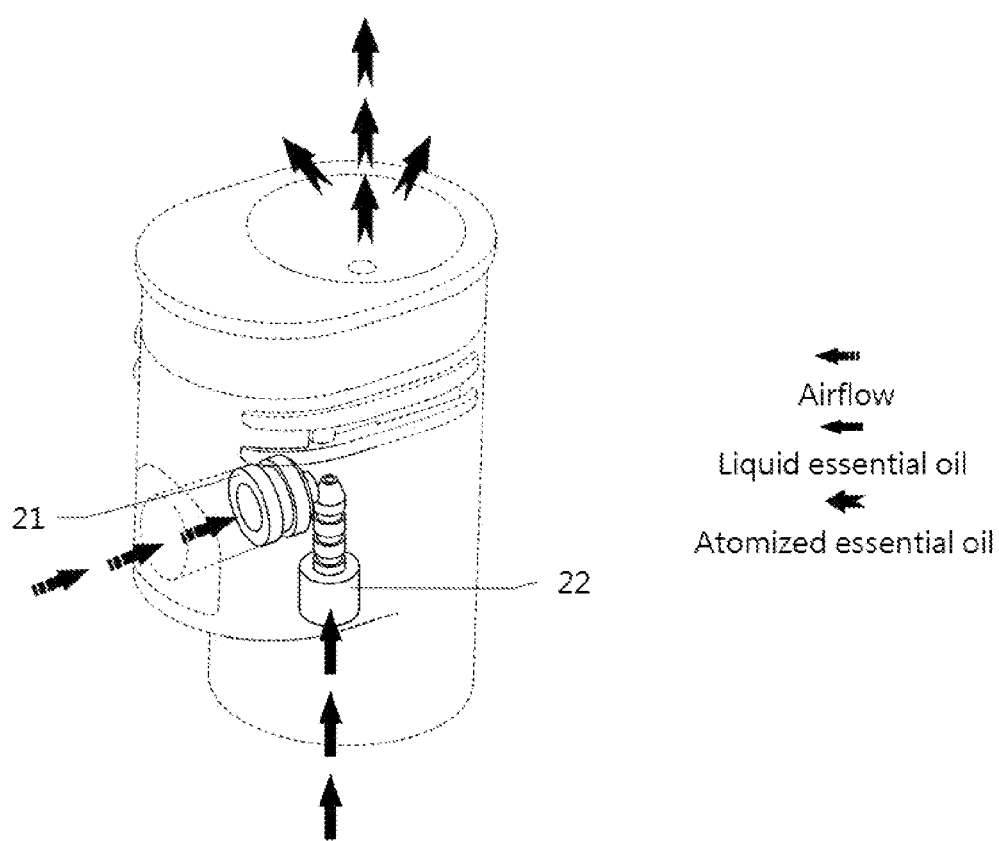
FIG. 5 is a schematic diagram of the essential oil nozzle and the air nozzle of the aroma diffuser of the present invention.

By reference to FIG. 1 and FIG. 5, the air nozzle 21 is interconnected with the air inlet channel 23. The essential oil nozzle 22 is interconnected with the essential oil bottle 1 via the oil guide pipe 24. The outlet direction of the air nozzle 21 and the outlet direction of the essential oil nozzle 22 are perpendicular to each other. In this embodiment, the air nozzle 21 and the essential oil nozzle 22 are made of a stainless steel material. Compared with plastic or other materials, the essential nozzle 22 made of stainless steel can reduce inside attachment of the essential oil and prevent the nozzle from being blocked. On the other hand, stainless steel nozzles are higher in machining precision, and are unlikely to deform and have a guaranteed consistency.

An aerial fog generation and diffusion process is as follows: airflow of compressed air is input into the air nozzle 21 through the air inlet channel 23 and is jetted out at a high speed by the air nozzle 21 to form a low pressure at the outlet position of the air nozzle 21; because the essential oil nozzle 22 is positioned below the air nozzle 21, and the exhaust direction of airflow of the air nozzle 21 is perpendicular to the jet direction of essential oil jetted from the essential oil nozzle 22, the low pressure area is just positioned above the essential oil nozzle 22, so that the essential oil in the essential oil bottle 1 will be extracted through the oil guide pipe 24 interconnected with the essential oil nozzle 22 according to the Venturi effect. The extracted essential oil will be atomized by the high-speed airflow. Under the driving the airflow, the atomized essential oil passes through the circular-arc-shaped first intake backflow channel 30 and second intake backflow channel 31 respectively. In this process, a part of atomized essential oil will be converted into liquid essential oil and flow back to the gasification cavity 20 through the first intake backflow channel 30 and the second intake backflow channel 31 and then flow back to the essential oil bottle 1 through the annular protruding portion 26 on the bottom of the gasification cavity 20. Under the driving of the airflow, the atomized essential oil flows out from the fog outlet 33, and is then diffused out of the aroma diffuser through the aroma diffusion hole 41 of the gasification cavity cover 4.

It is clear to the persons of ordinary skills in the pertinent art that transformations and improvements can be made to the present invention but these transformation and improvements do not depart from the conception of the present invention and should fall within the protection scope of the present invention. Therefore, the protection scope of the present invention is defined by the claims.

What is claimed is:

1. A pump type aroma diffuser, comprising:
   an essential oil bottle for containing essential oil;
   a gasification assembly connected with an open end of the essential oil bottle, the gasification assembly comprising a gasification cavity and an air nozzle and an essential oil nozzle which are installed on a cavity wall of the gasification cavity, the air nozzle and the essential oil nozzle are interconnected with the gasification cavity; and
   a guide assembly covering the gasification cavity for guiding aroma, wherein the guide assembly comprises a concentrated fog outlet for exhausting aroma, the guide assembly further comprising a first intake backflow channel and a second intake backflow channel which extend from the concentrated fog outlet to two different directions, tail ends of the first intake backflow channel and the second intake backflow channel extending into the gasification cavity.

2. The pump type aroma diffuser according to claim 1 further comprising a gasification cavity cover which covers the gasification assembly and the guide assembly and is used for sealing, wherein the gasification cavity cover has a cover plate, the cover plate having an aroma diffusion hole, aroma being diffused out of the pump type aroma diffuser from the aroma diffusion hole.

3. The pump type aroma diffuser according to claim 2, wherein the gasification cavity cover also comprises a first annular sealing layer and a second annular sealing layer which extend out from one side of the cover plate, the first sealing layer being configured to seal the guide assembly and the second sealing layer being configured to seal the gasification assembly.

4. The pump type aroma diffuser according to claim 1, wherein the guide assembly comprises a support plate covering the gasification cavity and a sleeve installed on the support plate and close to one side of the gasification cavity cover, the concentrated fog outlet being located at an inner wall of the sleeve.

5. The pump type aroma diffuser according to claim 4, wherein the support plate comprises a first plate and a second plate which are butted with each other, the sleeve being installed on the second plate, the first intake backflow channel and the second intake backflow channel respectively penetrating through the first plate and the second plate in a circular arc shape from both sides of the first plate, the first intake backflow channel and the second intake backflow channel being interconnected with the concentrated fog outlet on the inner wall of the sleeve.

6. The pump type aroma diffuser according to claim 1, wherein one end, which is interconnected with the gasification cavity, of the first intake backflow channel has a first intake backflow hole; one end, which is interconnected with the gasification cavity, of the second intake backflow channel has a second intake backflow hole; and positions of the first intake backflow hole and the second intake backflow holes are interlaced with each other.

7. The pump type aroma diffuser according to claim 1, wherein bottom of the gasification cavity has an annular protruding portion which extends into the open end of the essential oil bottle and is butted with the open end of the essential oil bottle, so that a part of non-gasified essential oil can flow back to the essential oil bottle.

8. The pump type aroma diffuser according to claim 1, wherein the gasification assembly also comprises an oil guide pipe disposed in the essential oil bottle, one end of the oil guide pipe being connected with the essential oil nozzle and another end of the oil guide pipe being inserted into bottom of the essential oil bottle.

9. The pump type aroma diffuser according to claim 1, wherein the gasification assembly also comprises a mounting wall for the essential oil bottle to be mounted on, outer side surface of the open end of the essential oil bottle having first threads, inner side of the mounting wall having corresponding second threads, the open end of the essential oil bottle being connected to the mounting wall via threaded connection.

10. The pump type aroma diffuser according to claim 1, wherein the air nozzle is interconnected with an air inlet channel, the essential oil nozzle being interconnected with the essential oil bottle through the oil guide pipe, exhaust direction of airflow of the air nozzle being perpendicular to the jet direction of essential oil jetted from the essential oil nozzle, the air nozzle and/or the essential oil nozzle being made of stainless steel.

\* \* \* \* \*